(12) United States Patent
Hebeisen et al.

(10) Patent No.: US 6,232,306 B1
(45) Date of Patent: May 15, 2001

(54) DERIVATIVES OF 3-(2-OXO-[1,3']BIPYRROLIDINYL-3-YLIDENEMETHYL)-CEPHAMS

(75) Inventors: Paul Hebeisen, Basel (CH); Christian Hubschwerlen, Durmenach; Jean-Luc Specklin, Kembs-Schaferhof, both of (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/332,811

(22) Filed: Jun. 14, 1999

Related U.S. Application Data

(63) Continuation-in-part of application No. 09/315,715, filed on May 20, 1999.

(30) Foreign Application Priority Data

Jun. 15, 1998 (EP) .................................................. 98110888
Sep. 10, 1998 (EP) .................................................. 98117099

(51) Int. Cl.[7] ...................... C07D 501/24; A61K 31/546; A61P 31/04
(52) U.S. Cl. ............................................. 514/202; 540/222
(58) Field of Search ............................. 514/202; 540/222

(56) References Cited

U.S. PATENT DOCUMENTS

| 5,466,811 | 11/1995 | Alexander | 546/283 |
| 5,610,314 | 3/1997 | Cheng et al. | 549/228 |
| 5,981,519 | * 11/1999 | Angehrn | 514/202 |

FOREIGN PATENT DOCUMENTS

| 0 841 339 | 5/1998 | (EP) . |
| 0 849 269 | 6/1998 | (EP) . |

OTHER PUBLICATIONS

Jose Alexander et al., Journal of Medicinal Chemistry, 39(2):480–486 (1996).
Zhong Li et al., Bioorganic and Medicinal Chemistry Letters, 7(22):2909–2912 (1997).
Christian Hubschwerlen et al., The Journal of Antibiotics, 45(8):1358–1364 (1992).

* cited by examiner

Primary Examiner—Mark L. Berch
(74) Attorney, Agent, or Firm—George W. Johnston; Patricia S. Rocha-Tramaloni; Eileen M. Ebel

(57) ABSTRACT

The present invention provides compounds of formula I

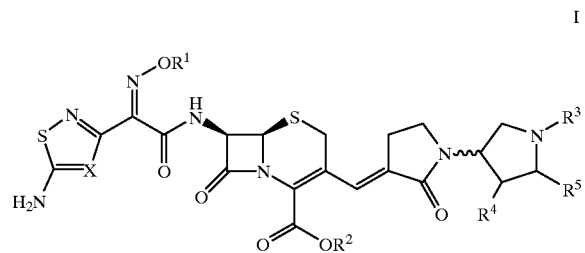

wherein $R^1$ is hydrogen, $C_{1-6}$-alkyl, $C_{1-6}$-alkyl substituted by fluoro, or $C_{3-6}$-cycloalkyl;

$R^2$ is hydrogen or a substituent selected from the group consisting of $-CH_2C(=CHR)-COOR$, $-CH_2OCOR$, $-CH(R)OCOR$, $-CH(R)OCOOR$, $-CH(OCOR)OCOR$, $-CH_2COCH_2OCOR$ and

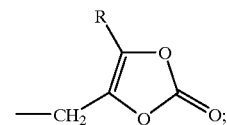

$R^3$ is hydrogen or a substituent selected from the group consisting of $-CH_2C(=CH_2)-COOR$, $-COOCH_2C(=CHR)-COOR$, $-COOCH_2OCOR$, $-COOCH(R)OCOR$, $-COOCH(R)OCOOR$, $-COOCH(OCOR)OCOR$, $-COOCH_2COCH_2OCOR$, and

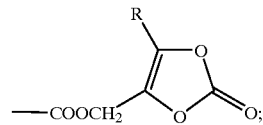

with the proviso that one of $R^2$ and $R^3$ is hydrogen and the other is not hydrogen, R is hydrogen or $C_{1-6}$-alkyl;

$R^4$ is hydrogen or hydroxy, $R^5$ is hydrogen or ω-hydroxyalkyl; and

X is CH or N, pharmaceutically acceptable salts of the compounds and hydrates of the compounds and of their salts.

9 Claims, No Drawings

DERIVATIVES OF 3-(2-OXO-[1,3']BIPYRROLIDINYL-3-YLIDENEMETHYL)-CEPHAMS

RELATION BACK UNDER 35 U.S.C. § 120

This is a continuation in part of copending application Ser. No. 09/315,715 filed on May 20, 1999.

FIELD OF THE INVENTION

The present invention is related to antibacterial compounds.

BACKGROUND OF THE INVENTION

Compounds of formula A

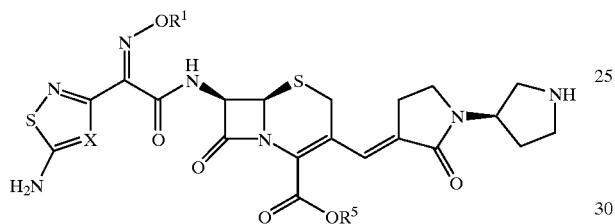

A wherein
- $R^1$ is hydrogen, $C_{1-6}$-alkyl, $C_{1-6}$-alkyl substituted by fluoro, or $C_{3-6}$-cycloalkyl;
- X is CH or N, and
- $R^5$ is hydrogen, and pharmaceutically acceptable salts thereof, especially (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid, are potent antibacterial agents with activity against methicillin resistant staphylococci, both in vitro and in vivo. However, these compounds have limited solubility, not allowing bolus injections. It is therefore necessary to find derivatives of the compounds A to render these compounds suitable for parenteral and intramuscular application.

From J. Med. Chem. (1996), 39(2), 480–6; U.S. Pat. No. 5,466,81 1; Bioorganic and Medicinal Chem. Left. 1997,7, 2909–2912; U.S. Pat. No. 5,610,314 (oxodioxolenyl)methyl carbamates are known to form derivatives of amines e.g. for fibrinogen receptor antagonists, ampicillin, norfloxacin and other pharmaceuticals. Furthermore, 2-(alkyloxycarbonyl)-2-alkylideneethyl esters have been described as prodrugs of carboxylic acids for cephalosporins, J. Antibiot. (1992), 45(8), 1358–64. Both types of derivatives have been used to improve the oral bioavailability of the corresponding drugs.

SUMMARY OF THE INVENTION

The present invention is concerned with new compounds of formula I

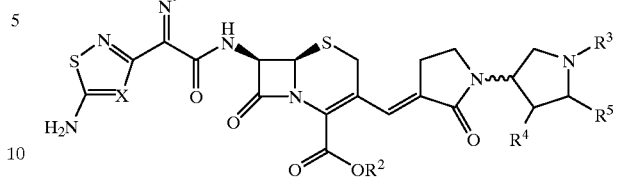

I wherein
- $R^1$ is hydrogen, $C_{1-6}$-alkyl, $C_{1-6}$-alkyl substituted by fluoro, or $C_{3-6}$-cycloalkyl;
- $R^2$ is hydrogen or a substituent selected from the group consisting of —CH$_2$C(=CHR)—COOR, —CH$_2$OCOR, —CH(R)OCOR, —CH(R)OCOOR, —CH(OCOR)OCOR, —CH$_2$COCH$_2$OCOR and

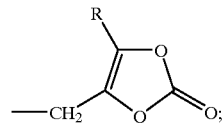

- $R^3$ is hydrogen or a substituent selected from the group consisting of —CH$_2$C(=CH$_2$)—COOR, —COOCH$_2$C(=CHR)—COOR, —COOCH$_2$OCOR, —COOCH(R)OCOR, —COOCH(R)OCOOR, —COOCH(OCOR)OCOR, —COOCH$_2$COCH$_2$OCOR, and

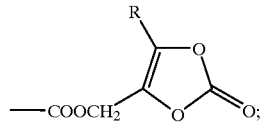

with the proviso that one of $R^2$ and $R^3$ is hydrogen and the other is not hydrogen,
- R is hydrogen or $C_{1-6}$-alkyl;
- $R^4$ is hydrogen or hydroxy,
- $R^5$ is hydrogen or ω-hydroxyalkyl; and
- X is CH or N, pharmaceutically acceptable salts of the compounds and hydrates of the compounds of formula I and of their salts.

The present invention provides pharmaceutical preparations of a compound of formula I or the salts of the compounds or hydrates of the compounds or of their salts, and an inert carrier.

The present invention also provides for the use of a compound of formula I or the salts of the compounds or hydrates of the compounds or their salts, in the treatment or prophylaxis of infectious diseases.

DETAILED DESCRIPTION OF THE INVENTION

It has now been found that the compounds of formula I exhibit good solubility in water and in buffers at physiological pH. In vitro and in vivo they were readily converted to compounds of formula A. The formula I compounds can therefore be used for parenteral and intramuscular dosage application forms. The invention is thus also concerned with pharmaceutical preparations containing a compound of formula I and a therapeutically inert carrier.

As used herein "pharmaceutically acceptable salts" useful in this invention include salts derived from metals, salts derived from amino acids and salts of mineral or organic acids. Examples of preferred metal salts are those derived from the alkali metals, for example, lithium (Li+), sodium (Na+) and potassium (K+). Especially preferred is sodium. Other salts are derived from amino acids such as, for example, salts with arginine or lysine. Examples of salts of mineral acids are for example chlorides, sulphates or phosphates, and examples of salts of organic acids are mesylates (methylsulfonic acid salts), napsylates (naphthtene-2-sulfonic acid salts), besylates (benzenesulfonic acid salts), maleates, salicylates, tartrates, lactates, citrates, benzoates, succinates, acetates and the like. Especially preferred are chlorides, sulfates, phosphates, lactates and mesylates.

In the formulas represented herein, when substituents are illustrated as joined to the nucleus, a solid line (——) indicates that the substituent is in the β-orientation, that is, above the plane of the molecule, a broken line (·····) indicates that the substituent is in the α-orientation, that is, below the plane of the molecule, whereas the zigzagged line (⁓⁓⁓) indicates that the bond is either in α- or in β-orientation.

The terms "$C_{1-6}$-alkyl" and "$C_{1-6}$-alkyl substituted by fluoro" refer to both straight and branched chain saturated hydrocarbon groups having 1 to 6 and preferably 1 to 4 carbon atoms, for example, methyl, ethyl, n-propyl, isopropyl, tertiary butyl and the like. For "$C_{1-6}$-alkyl substituted by fluoro", a $C_{1-6}$ group is substituted by one or more fluorine atoms as, e.g., in fluoromethyl or trifluoromethyl.

As used herein, the term "ω-hydroxyalkyl" refers to both straight and branched chain saturated hydrocarbon groups as defined above bearing a hydroxy group in the terminal position, e.g. hydroxymethyl, 2-hydroxyethyl, 3-hydroxypropyl, preferably hydroxymethyl.

By the term "$C_{3-6}$-cycloalkyl" is meant a 3–6 membered saturated carbocyclic moiety, e.g., cyclopropyl, cyclobutyl, cyclopentyl and cyclohexyl, in particular cyclopentyl.

Especially preferred compounds of formula I are the compounds of formula

I-a

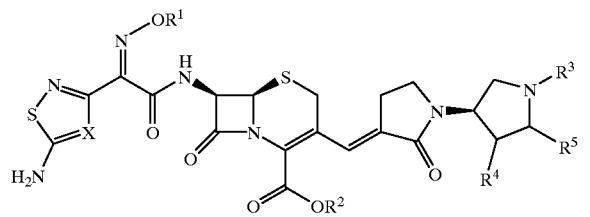

wherein, $R^1$, $R^2$, $R^3$, and X are as defined above and $R^4$ and $R^5$ are hydrogen, as well as pharmaceutically acceptable salts of said compounds and hydrates of the compounds of formula I-a and of their salts.

Further preferred compounds are epimers and diastereoisomers of formula I-a.

Preferred compounds of formula I and formula I-a are compounds wherein $R^1$ is hydrogen, X is N and $R^2$ is hydrogen and $R^3$ is a group chosen from —$CH_2C(=CH_2)$— $COOCH_2CH_3$, —COO—$CH_2C(=CHCH_2CH_3)$— $COOCH_2CH(CH_3)_2$, and particularly

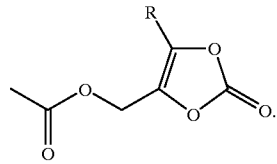

Further preferred compounds of formula I are compounds wherein $R^1$ and $R^3$ are hydrogen, X is N and $R^2$ is a group chosen from —$CH_2C(=CHCH_2CH_3)$—$COOCH_2CH(CH_3)_2$, —$CH_2C(=CH_2)$—$COOCH_2CH_3$, —$CH_2OCOC(CH_3)_3$, —$CH(CH_3)OCOCH_3$, —$CH(CH_3)OCOOCH_2CH_3$, —$CH(OCOCH_3)OCOCH_3$, —$CH_2COCH_2OCOCH_3$, and

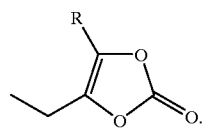

Especially preferred compounds of formula I and I-a are:

(6R,7R)-7-[(Z)-2-(5-amino-[1,2,4]thiadiazol-3-yl)-2-hydroxyimino-acetylamino]-3-[(E)-(R)-1'-(5-methyl-2-oxo-[1,3]dioxol4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid;

(6R,7R)-7-[(Z)-2-(5-amino-[1,2,4]thiadiazol-3-yl)-2-hydroxyimino-acetylamino]-3-[(E)-(R)-1'-(5-ethyl-2-oxo-[1,3]dioxol4-ylmethoxycarbonyl)-2-oxo-[1,3']bipyrrolidinyl-3-ylidenemethyl]-8-oxo5-thia-1-aza-bicyclo[4.2.0]oct-2-ene-2-carboxylic acid sodium salt (1:1);

(6R,7R)-7-[(Z)-2-(5-Amino-[1,2,4]thiadiazol-3yl)-2-hydroxyimino-acetylamino]-3-[(E)-(R)-1'-(2-oxo-5-propyl -[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1: 1);

(6R,7R)-7-[(Z)-2-(5-amino-[1,2,4]thiadiazol-3-yl)-2-hydroxyimino-acetylamino]-3-[(E)-(R)-1'-(5-isopropyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1);

(6R,7R)-7-[(Z)-2-(5-amino-[1,2,4]thiadiazol-3-yl)-2-hydroxyimino-acetylamino]-3-[(E)-(R)-1'-(5-tert-butyl-2-oxo-[1,3]dioxol4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1);

(6R,7R)-7-[(Z)-2-(5-Amino-[1,2,4]thiadiazol-3-yl)-2-hydroxyimino-acetylamino]-3-[(E)-(R)-1'-(E-2-isobutoxycarbonyl-pent-2-enyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1);

(6R,7R)-7-[(Z)-2-(5-Amino-[1,2,4]thiadiazol-3-yl)-2-hydroxyimino-acetylamino]-3-[(E)-(R)-1'-(2-ethoxycarbonyl-allyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1);

(6R,7R)-7-[(Z)-2-(5-Amino-[1,2,4]thiadiazol-3-yl)-2-hydroxyimino-acetylamino]-3-[(E)-5'-hydroxymethyl-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt; and (6R,7R)-7-[(Z)-2-(5-amino-[1,2,4]thiadiazol-3-yl)-2-hydroxyimino-acetylamino]-3-[(E)-(3'S,4'S)- and -(3'R,4'R)-4'-hydroxy-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt.

The compounds of formula I and I-a as well as their salts can be hydrated. The hydration can be effected in the course of the manufacturing process or can occur gradually as a result of hygroscopic properties of an initially anhydrous product.

The compounds of the present invention are useful as antibiotics having potent and broad antibacterial activity; especially against methicillin resistant Staphylococci (MRSA) and Pseudomonas aeruginosa.

The products in accordance with the invention can be used as medicaments, for example, in the form of pharmaceutical preparations for parenteral administration, and for this purpose are preferably made into preparations as lyophilisates or dry powders for dilution with customary inert carriers, such as, for example, water, isotonic common salt, carbohydrate (e.g. glucose) solution etc. The parenteral preparation are advantageously formulated as injectibles, e.g., for intramuscular administration.

Depending on the nature of the pharmacologically active compound, the pharmaceutical preparations can be formulated for the prevention and treatment of infectious diseases in mammals, humans and non-humans. A daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

The compounds of the formula I and I-a in accordance with the invention as well as their pharmaceutically acceptable salts, hydrates, or readily hydrolyzable esters can for example be prepared in accordance to procedures given below:

Compounds of formula I and I-a wherein $R^2$ is hydrogen and $R^3$ is a group —COOCH$_2$C(=CHR)—COOR, —COOCH$_2$OCOR, —COOCH(R)OCOR, —COOCH(R)OCOOR, —COOCH(OCOR)OCOR, —COOCH$_2$COCH$_2$OCOR or

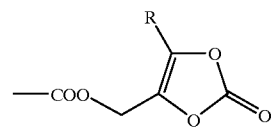

can be prepared according to Scheme 1 by acylation of compounds of formula A with the corresponding carbonic acid 4-nitrophenyl ester.

Scheme 1

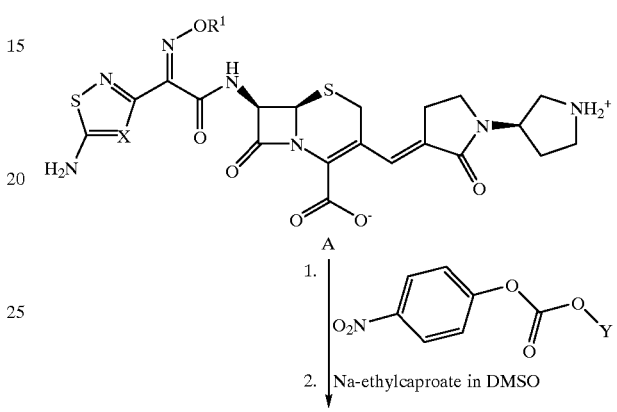

wherein $R^1$ and R are as defined above and Y is a group —CH$_2$C(=CHR)—COOR, —CH$_2$OCOR, —CH(R)OCOR, —CH(R)OCOOR, —CH(OCOR)OCOR, —CH$_2$CO CH$_2$OCOR, or

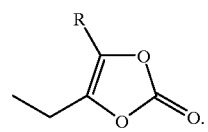

For the preparation of compounds of formula I and I-a wherein $R^3$ is —CH$_2$C(=CH$_2$)—COOR a compound of formula A is reacted with 2-(4-nitro-phenoxycarbonyloxymethyl)-acrylic acid ethyl ester. This reaction proceeds with loss of carbon dioxide, cf. scheme 2:

Scheme 2

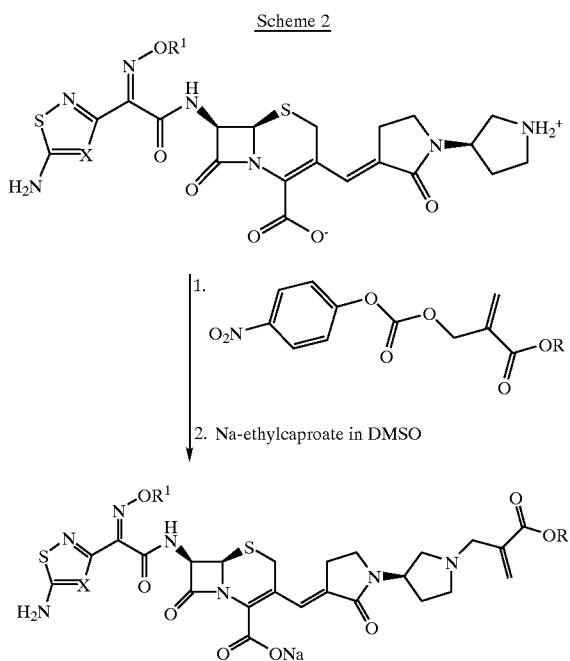

The synthesis of the compounds of formula I and I-a, wherein $R^3$ is hydrogen, (Scheme 3) is accomplished via alkylation of the carboxylate, preferably at the stage of the fully protected compound of formula A. Protecting groups for $R^1$ are preferably the trityl, and in position $R^3$ tert.-butyloxycarbonyl (BOC). Removal of the tert.-butyloxycarbonyl and trityl-protecting groups is accomplished by conventional methods and the desired compounds of formula I and I-a are isolated as the hydrochloride salts by precipitation from dioxane.

Scheme 3

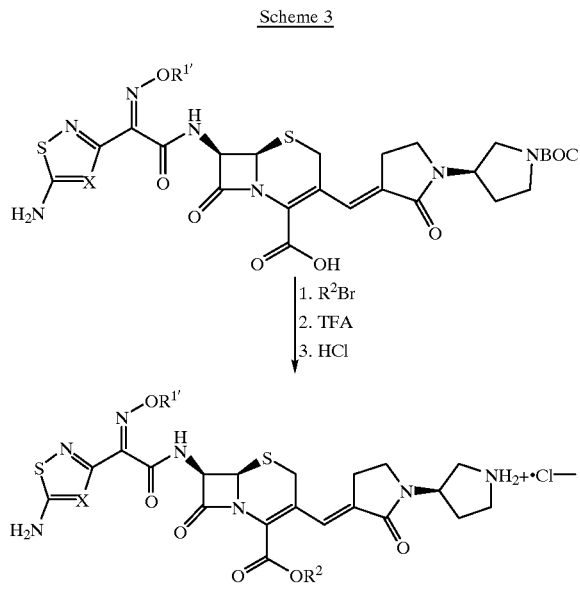

wherein $R^{1'}$ is $C_{1-6}$-alkyl, $C_{1-6}$-alkyl substituted by fluoro, or $C_{3-6}$-cycloalkyl or a protecting group, preferably trityl, and BOC is tert.-butyloxycarbonyl.

Compounds of formula A are known compounds and can be prepared according to the methods described in EP 0 849 269.

The alkylating agents, i.e. the compounds $R^2Br$ or $R^2Cl$ are known compounds; some are commercially available.

The following examples further illustrate the invention, however, without limiting its scope.

Examples 1.1. Synthesis of (6R,7R)-7-[(Z)-2-(5-amino-[1,2,4]thiadiazol-3-yl)-2-hydroxyiminoacetylamino]-3-[(E)-(R)-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid

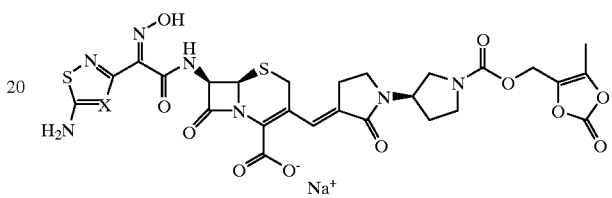

To a solution of 13.2 g (44.72 mmol) of carbonic acid 5-methyl-2-oxo-[1,3]dioxol4-ylmethyl ester 4-nitro-phenyl ester in 200 ml of dimethylsulfoxide are added 20.0 g of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid. The mixture is stirred under argon at room temperature for 4 hours and 1000 ml of acetone are added. The slightly turbid solution is clarified by filtration over a fluted filter. To the clear motherliquour are added 34.0 ml (34 mmol) of a 1N solution of sodium-2-ethylcaproate in acetone at room temperature during 20 minutes. The slightly yellow suspension is stirred for 10 minutes at room temperature, the solid is collected by filtration, washed with 1000 ml of acetone and 1000 ml of n-pentane and dried under high vacuum. The product is suspended in 600 ml of acetone and stirred at room temperature for 2 hours. The product is collected by filtration and dried under high vacuum to yield 23.94 g of the title compound as an off-white powder.

MS(ISP): $M+H^+=691.3$; $M+NH_4^+=708.2$; $M+Na^+=713.1$.

In a similar manner, the following carbamates are prepared from the corresponding mixed carbonates:

1.2. (6R,7R)-7-[(Z)-2-(5-Amino-[1,2,4]thiadiazol-3-yl)-2-hydroxyimino-acetylamino]-3-[(E)-(R)-1'-(5-ethyl-2-oxo-[1,3]dioxol-4-ylmethoxycarbonyl)-2-oxo-[1,3']-bipyrrolidinyl-3-ylidenemethyl]-8-oxo-5-thia-1-aza-bicyclo[4.2.0]oct-2-ene-2-carboxylic acid sodium salt (1:1)

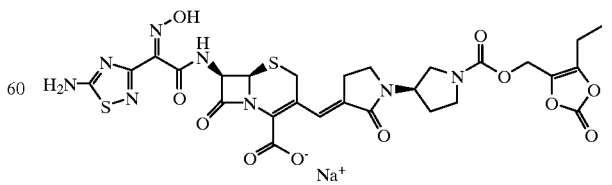

MS (ISP): $M+H^+=705.2$, $M+NH_4^+=722.3$, $M+Na^+=727.2$.

1.3. (6R,7R)-7-[(Z)-2-(5-Amino-[1,2,4]thiadiazol-3-yl)-2-hydroxyimino-acetylamino]-3-[(E)-(R)-1'-(2-oxo-5-propyl-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1)

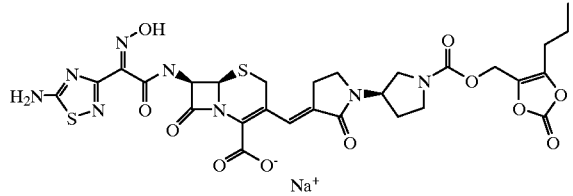

MS (ISP): M+H⁺=719.3, M+NH₄⁺=736.2, M+Na⁺=741.2.

1.4. (6R,7R)-7-[(Z)-2-(5-Amino-[1,2,4]thiadiazol-3-yl)-2-hydroxyimino-acetylamino]-3-[(E)-(R)-1'-(5-isopropyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1)

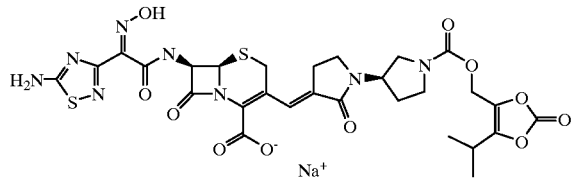

MS (ISP): M+H⁺=719.3, M+NH₄⁺=736.2, M+Na⁺=741.2.

1.5. (6R,7R)-7-[(Z)-2-(5-Amino-[1,2,4]thiadiazol-3-yl)-2-hydroxyimino-acetylamino]-3-[(E)-(R)-1'-(5-tert-butyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1)

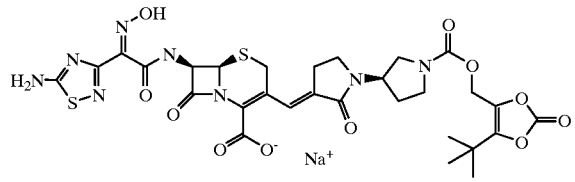

MS (ISP): M+H⁺=733.2, M+NH₄⁺=750.4.

1.6. (6R,7R)-7-[(Z)-2-(5-Amino-[1,2,4]thiadiazol-3-yl)-2-hydroxyimino-acetylamino]-3-[(E)-(R)-1'-(E-2-isobutoxycarbonyl-pent-2-enyloxycarbonyl)-2-oxo-[1,3']bipyrrolidinyl-3-ylidenemethyl]-8-oxo-5-thia-1-aza-bicyclo[4.2.0]oct-2ene-2-carboxylic acid sodium salt (1:1)

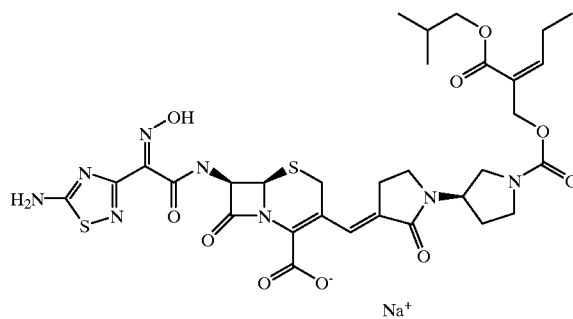

MS (ISP): M+H⁺=747.4, M+NH₄⁺=764.3, M+Na⁺=769.3.

1.7. (6R,7R)-7-[(Z)-2-(5-Amino-[1,2,4]thiadiazol-3-yl)-2-hydroxyimino-acetylamino]-3-[(E)-(R)-1'-(2-ethoxycarbonyl-allyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1)

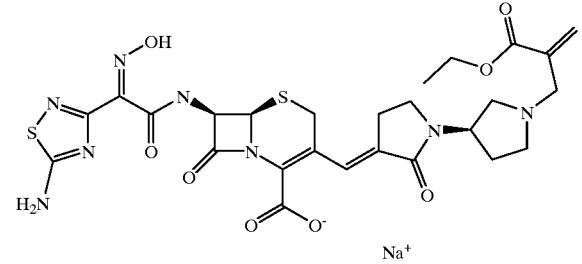

MS (ISP): M+H⁺=647.4.

1.8. (6R,7R)-7-[(Z)-2-(5-Amino-[1,2,4]thiadiazol-3-yl)-2-hydroxyimino-acetylamino]-3-[(E)-(3'R,5'S)-5'-hydroxymethyl-1'-(5-methyl-2-oxo-[1,3]dioxol4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt

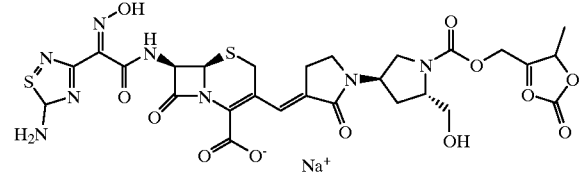

MS(ISP): M+H⁺=721.3; M+NH4⁺=738.2; M+Na⁺=743.2.

1.9 1:1 Mixture of (6R,7R)-7-[(Z)-2-(5-amino-[1,2,4]thiadiazol-3-yl)-2-hydroxyimino-acetylamino]-3-[(E)-(3'S,4'S)- and -(3'R,4'R)-4'-hydroxy-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid sodium salt (1:1)

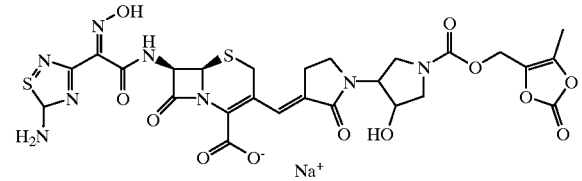

MS(ISN): M-H⁺=705.3.

Preparation of the starting materials for examples 1.7. and 1.6.:

a) 2-(4-Nitro-phenoxycarbonyloxymethyl)-acrylic acid ethyl ester

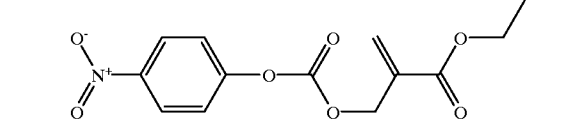

A mixture of 2.60 g of 2-hydroxymethyl-acrylic acid ethyl ester (0.020 mol) and 4.0 g of 4-nitrophenyl-chloroformate (0.020 mol) in 70 ml dichloromethane is treated with a solution of 5.5 ml (0.030 mol) of ethyl-diisopropylamine in 55 ml of dichloromethane at 0° C. for two hours. The mixture is hydrolyzed with 10% potassium bicarbonate, the phases are separated and the product contained in the organic phase is purified by chromatography on silica gel using a 4:1 mixture of n-hexane and ethyl acetate as eluent. The product fractions are collected and evaporated yielding 3.5 g (60%) of the title compound as a white crystalline solid with melting point 42–43° C. after crystallisation from t-butylmethyl ether and n-hexane.

b) 2-(4-Nitro-phenoxycarbonyloxymethyl)-pent-2-enoic acid isobutyl ester

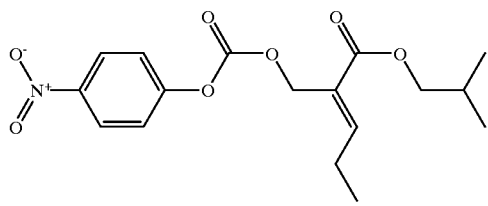

is prepared according to the procedure described above. A yellowish oil is obtained.

MS (EI): M+H$^+$=352 M-C$_4$H$_7$O=278.

Example 2

2.1. a) Synthesis of (6R,7R)-7-[(Z)-2-(5-amino-[1,2,4]thiadiazol-3-yl)-2-trityloxyimino-acetylamino]-3-[(E)-(R)-1'-tert-butoxycarbonyl-2-oxo-[1,3']bipyrrolidinyl-3-ylidenemethyl]8-oxo-5-thia-1-aza-bicyclo[4.2.0]oct-2-ene-2-carboxylic acid

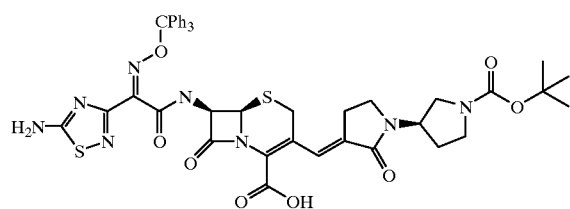

To a solution of 1.67 g (1.965 mmol) of (6R,7R)-7-[(Z)-2-(5-amino-[1,2,4]thiadiazol-3-yl)-2-trityloxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid hydrochloride salt (1:2) in 20.0 ml of dimethylformamide are added 0.56 ml (4.00 mmol) of triethylamine and 0.554 g di-tert-butyldicarbonate and the mixture is stirred at room temperature for 1.5 hours. The mixture is diluted with 500 ml of ethyl acetate and 100 ml water. The pH is adjusted to 2 by the addition of 1N hydrochloric acid. The phases are separated and the organic phase is washed twice with 100 ml of water, clarified by filtration over a fluted filter and concentrated. 100 ml of diethyl ether are added and the resulting suspension is stirred at room temperature for 1 hour. The solid is collected by filtration, washed with diethyl ether and dried, yielding 1.31 g (76%) of the title compound as a beige powder.

MS (ISP): (M+H)$^+$=877.4 (M+NH$_4$)$^+$=894.4 (M+Na)$^+$=899.4.

b) Synthesis of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid (E)-2-isobutoxycarbonyl-pent-2-enyl ester hydrochloride (1:1.6)

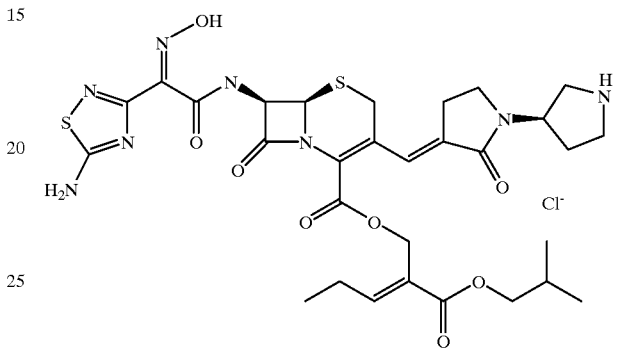

To a solution of 0.150 g (0.171 mmol) of (6R,7R)-7-[(Z)-2-(5-amino-[1,2,4]thiadiazol-3-yl)-2-trityloxyimino-acetylamino]-3-[(E)-(R)-1'-tert-butoxycarbonyl-2-oxo-[1,3']bipyrrolidinyl-3-ylidenemethyl]8-oxo-5-thia-1-aza-bicyclo[4.2.0]oct-2-ene-2-carboxylic acid in 1 ml of dimethylsulfoxide are added 18.7 mg of (0.163 mmol) 1,1-3,3-tetramethyl guanidine and 64 mg (0.257 mmol) of isobutyl (Z)-2-(bromomethyl)-2-pentenoate, and the mixture is stirred at room temperature for 20 minutes. The solvent is evaporated under high vacuum and the residue purified by chromatography on MCI-gel using a gradient of 40 to 100% of acetonitrile in water as eluent. The product fractions are collected and the organic solvent is removed by evaporation. The product is extracted from the remaining aqueous phase with dichloromethane. The combined organic phases are dried over magnesium sulfate, evaporated to dryness and triturated with tert-butylmethyl ether to yield 130 mg (0.125 mmol) beige crystals with melting point 158–159° C. which are dissolved in 1.2 ml of dichloromethane. To this solution are added 0.0366 ml (0.23 mmol) of triethylsilane and 0.38 ml of trifluoroacetic acid at 0° C. and the mixture is stirred for 1 hour. To the resulting clear solution 2.0 ml of dioxane are added and the mixture is concentrated under vacuum. The residue is dissolved in 2.0 ml of dioxane and 0.182 ml of a 1.9 N solution of hydrochloric acid in dioxane are added with stirring at room temperature. The precipitate is collected by filtration washed with dioxane and acetone and dried yielding 85 mg of the title compound as beige crystals melting at 139–140° C. (dec). HPLC: 99.% (area) MS: M+H$^+$=703.3.

In a similar manner the following prodrug-ester compounds are prepared starting from the corresponding alkyl halides:

2.2. (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid 2,2-dimethyl-propionyloxymethyl ester hydrochloride

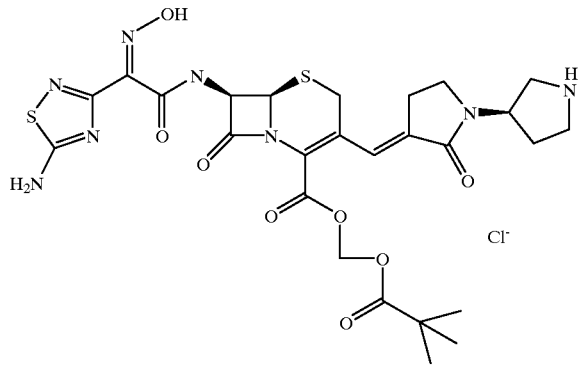

MS (ISP): M+H$^+$=649.3.

2.3. (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid 5-methyl-2-oxo-[1,3]dioxol-4-ylmethyl ester hydrochloride (1:1.5)

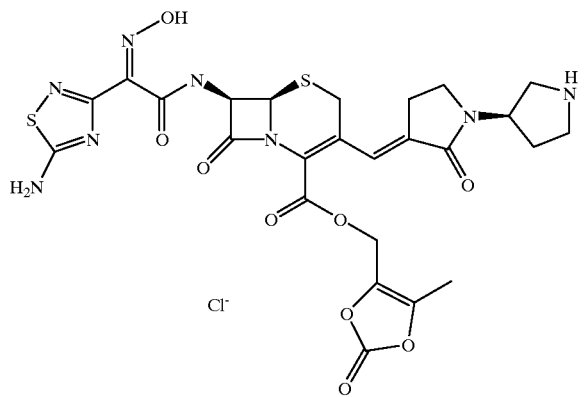

MS (ISP): M+H$^+$=647.3.

2.4. 1:1 Mixture of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid (R)- and (S)-1-acetoxy-ethyl ester hydrochloride (1:1.2)

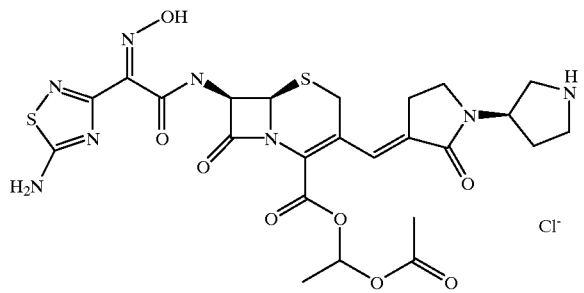

MS (ISP): M+H$^+$=621.3.

2.5. 1:1 Mixture of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid (R)- and (S)-1-ethoxycarbonyloxy-ethyl ester hydrochloride (1:1.4)

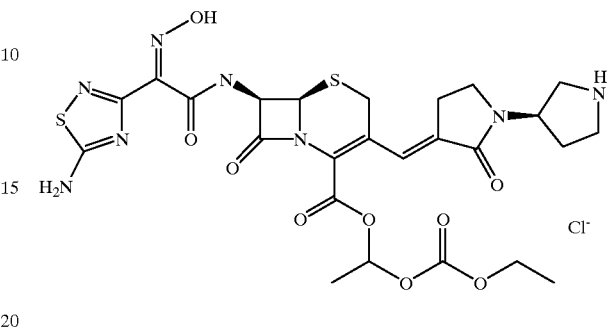

MS (ISP): M+H$^+$=651.2.

2.6. 1:1 Mixture of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid (R)- and (S)-1-acetoxy-2-oxo-propyl ester hydrochloride (1:1.4)

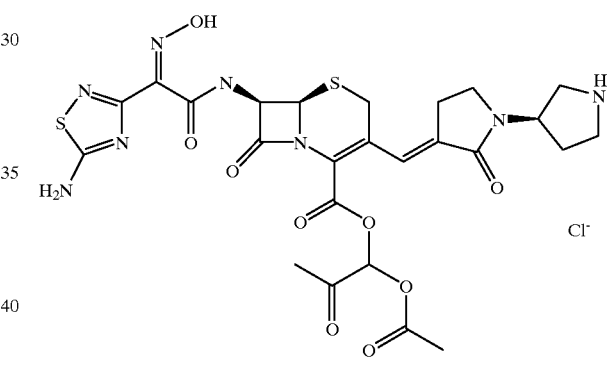

MS (ISP): M+H$^+$=649.

2.7. (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid 3-acetoxy-2-oxo-propyl ester hydrochloride (1:1.65)

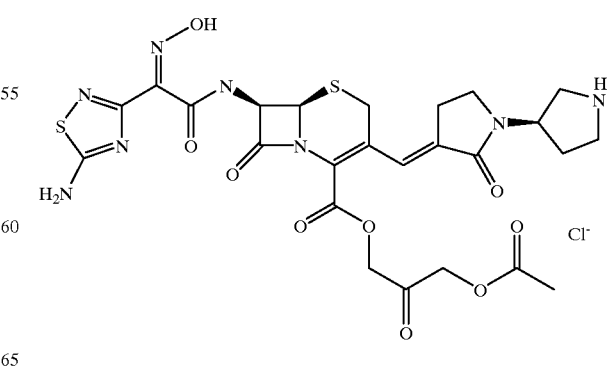

MS (ISP): M+H$^+$=649.2.

What is claimed is:

1. A compound of the formula:

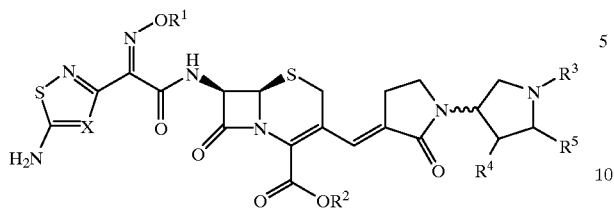

wherein $R^1$ is hydrogen, $C_{1-6}$-alkyl, $C_{1-6}$-alkyl substituted by fluoro, or $C_{3-6}$-cycloalkyl;

$R^2$ is hydrogen;

$R^3$ is a substituent selected from the group consisting of —CH$_2$C(=CH$_2$)—COOR, —COOCH$_2$C(=CHR)—COOR, —COOCH$_2$OCOR, —COOCH(R)OCOR, —COOCH(R)OCOOR, —COOCH(OCOR)OCOR, —COOCH$_2$COCH$_2$OCOR, and

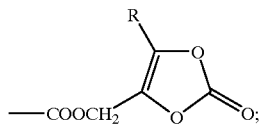

R is hydrogen or $C_{1-6}$-alkyl;

$R^4$ is hydrogen or hydroxy, $R^5$ is hydrogen or ω-hydroxyalkyl; and

X is CH or N, pharmaceutically acceptable salts of said compound, and hydrates of said compound and of said salts.

2. The compound according to claim 1, wherein said compound is of the

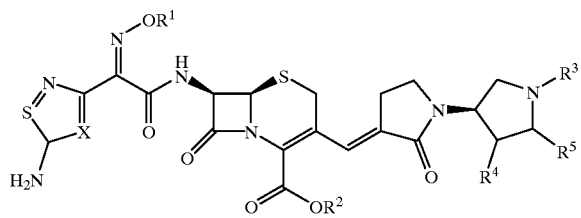

formula
wherein $R^4$ and $R^5$ are each hydrogen, and
pharmaceutically acceptable salts of said compound and hydrates of said compound and of said salts.

3. The compound according to claim 1, wherein $R^1$ is hydrogen, X is N, $R^2$ is hydrogen and $R^3$ is a substituent selected from the group consisting of —COO—CH$_2$C(=CHCH$_2$CH$_3$)—COOCH$_2$CH(CH$_3$)$_2$, —CH$_2$C(=CH$_2$)—COOCH$_2$CH$_3$, and

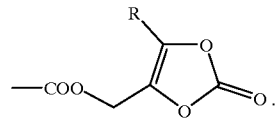

4. The compound according to claim 3, wherein $R^3$ is

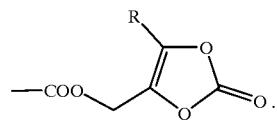

5. A method of use of the compound, salt or hydrate according to claim 1 in the treatment or prophylaxis of bacterial infection, comprising administering to a patient in need of treatment from about 10 mg to about 400 mg per day.

6. The compound according to claim 1, wherein the compound is (6R,7R)-7-[(Z)-2-(5-amino-[1,2,4]thiadiazol-3-yl)-2-hydroxyimino-acetylamino]- 3-[(E)-(R)-1'-(5-methyl-2-oxo-[1,3]dioxol4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid.

7. The compound according to claim 1, wherein the compound is (6R,7R)-7-[(Z)-2-(5-amino-[1,2,4]thiadiazol-3yl)-2-hydroxyimino-acetylamino]-3-[(E)-(R)-1'-(5-ethyl-2-oxo-[1,3]dioxol4-ylmethoxycarbonyl)-2-oxo-[1,3'] bipyrrolidinyl-3-ylidenemethyl]-8-oxo-5-thia-1-aza-bicyclo [4.2.0]oct-2-ene-2-carboxylic acid sodium salt (1:1).

8. A pharmaceutical preparation comprising the compound, salt or hydrate according to claim 1 and an inert carrier.

9. A method of use of the pharmaceutical preparation according to claim 8 in the treatment or prophylaxis of bacterial infection, comprising administering to a patient in need of treatment from about 10 mg to about 400 mg per day.

* * * * *